United States Patent
Chen et al.

(10) Patent No.: US 7,672,421 B2
(45) Date of Patent: Mar. 2, 2010

(54) REDUCTION OF STREAK ARTIFACTS IN LOW DOSE CT IMAGING THROUGH MULTI IMAGE COMPOUNDING

(75) Inventors: Yunqiang Chen, Plainsboro, NJ (US); Tong Fang, Morganville, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/539,665

(22) Filed: Oct. 9, 2006

(65) Prior Publication Data
US 2007/0140407 A1 Jun. 21, 2007

Related U.S. Application Data

(60) Provisional application No. 60/725,945, filed on Oct. 12, 2005.

(51) Int. Cl.
*A61B 6/00* (2006.01)
(52) U.S. Cl. .......................................................... 378/4
(58) Field of Classification Search ............... 378/4–20, 378/207, 901
See application file for complete search history.

(56) References Cited

U.S. PATENT DOCUMENTS

| | | | | |
|---|---|---|---|---|
| 4,709,333 A * | 11/1987 | Crawford | ..................... | 600/425 |
| 4,729,100 A * | 3/1988 | Tsujii | ............................ | 378/4 |
| 5,416,815 A * | 5/1995 | Hsieh | ............................ | 378/4 |
| 5,438,602 A * | 8/1995 | Crawford et al. | ................ | 378/4 |
| 5,933,471 A * | 8/1999 | Kalvin | ........................... | 378/4 |
| 6,028,908 A * | 2/2000 | Taguchi | ........................ | 378/15 |
| 6,035,012 A * | 3/2000 | Hsieh | ............................. | 378/4 |
| 6,038,278 A * | 3/2000 | Hsieh et al. | .................... | 378/15 |
| 6,101,236 A * | 8/2000 | Wang et al. | ..................... | 378/4 |
| 6,282,257 B1 * | 8/2001 | Basu et al. | ..................... | 378/15 |
| 6,332,035 B1 * | 12/2001 | Basu et al. | ................... | 382/128 |
| 6,351,548 B1 * | 2/2002 | Basu et al. | ................... | 382/128 |
| 6,426,988 B2 * | 7/2002 | Yamada et al. | ................. | 378/4 |
| 6,507,633 B1 * | 1/2003 | Elbakri et al. | .................. | 378/8 |
| 6,721,387 B1 * | 4/2004 | Naidu et al. | ................... | 378/8 |
| 6,754,298 B2 * | 6/2004 | Fessler | ........................... | 378/4 |
| 6,768,782 B1 * | 7/2004 | Hsieh et al. | ..................... | 378/8 |
| 6,775,352 B2 * | 8/2004 | Toth et al. | .................... | 378/108 |
| 6,845,142 B2 * | 1/2005 | Ohishi | ........................... | 378/8 |
| 6,850,586 B2 * | 2/2005 | Cahill | ............................ | 378/8 |
| 6,950,492 B2 * | 9/2005 | Besson | .......................... | 378/5 |
| 7,023,951 B2 * | 4/2006 | Man | .............................. | 378/8 |
| 7,113,569 B2 * | 9/2006 | Okumura et al. | ............ | 378/150 |

(Continued)

OTHER PUBLICATIONS

Bruyant et al., Streak Artifact Reduction in Filtered Backprojection Using a Level Line-Based Interpolation Method, J Nucl Med 2000; 41; pp. 1913-1919.*

(Continued)

*Primary Examiner*—Edward J Glick
*Assistant Examiner*—Alexander H Taningco

(57) ABSTRACT

Disclosed is a method and system for constructing, from a computerized tomography (CT) scan, an image relating to a physical structure. Projection data associated with the image is obtained and divided into a plurality of subsets. Filtered back projection (FBP) is then applied to each subset in the plurality of subsets. The image is constructed based on the application of the FBP to each subset in the plurality of subsets.

27 Claims, 6 Drawing Sheets

U.S. PATENT DOCUMENTS

2003/0161443 A1*  8/2003   Xiao et al. .................. 378/210
2004/0264625 A1* 12/2004   Basu et al. ...................... 378/4
2005/0058240 A1*  3/2005   Claus ........................... 378/22
2005/0105693 A1*  5/2005   Zhao et al. .................. 378/210
2006/0115040 A1*  6/2006   Chen ............................ 378/19

OTHER PUBLICATIONS

Alvino, et al. "Tomographic Reconstruction of Piecewise Smooth Images", Proc. of the 2004 IEEE Computer Society Conference on Computer Vision and Pattern Recognition (CVPR'04), vol. 1, pp. 576-581, 2004.

Bockisch, et al. "Positron Emission Tomography/Computed Tomography-Imaging Protocols, Artifacts, and Pitfalls", Modular Imaging and Biology, vol. 6, No. 4, pp. 188-199, 2004.

Williamson, et al., "Prospects for Quantitative CT Imaging in the Presence of Foreign Metal Bodies Using Statistical Image Reconstruction", Proc. of the IEEE International Symposium on Biomedical Imaging, pp. 649-652, 2002.

* cited by examiner

REDUCTION OF STREAK ARTIFACTS IN LOW DOSE CT IMAGING THROUGH MULTI IMAGE COMPOUNDING

This application claims the benefit of U.S. Provisional Application No. 60/725,945, filed Oct. 12, 2005, which is incorporated herein by reference.

BACKGROUND OF THE INVENTION

Computer Axial Tomography (CAT), sometimes known generally as Computerized Tomography (CT), is used in many applications, especially medical radiology, to obtain two or three dimensional views of the interior of three dimensional bodies (CT or CAT Scans). The technique involves subjecting a three dimensional body to radiation that enters the body from many different angles. The amount of radiation that is scattered or reflected by the body is then detected as a function of the angle of scattering. The scattered data is then analyzed to construct an image of the interior of the body. A two dimensional "slice" of the interior can be "reconstructed", for example on a screen, and viewed. The slice can be reconstructed for any desired angle of intersection with the body.

While computerized tomography is well known, various specific mathematical reconstruction algorithms have been proposed to construct the image from the scattered radiation. However, it is becoming more challenging for known conventional reconstruction methods to meet the stringent constraints of current imaging applications. For example, the rates at which the impinging radiation beam scans the body has increased dramatically over the years, and the impinging radiation dosage has dropped significantly, especially in medical applications, because of patient safety concerns.

Two of the most common reconstruction algorithms that were developed to meet the stringent constraints of current imaging applications are the Filtered Back Projection method (FBP, sometimes written Filtered Backprojection method) and the Iterative Reconstruction Method (IR). In FBP, as a radiation detector rotates around the body being exposed to radiation, it detects and creates a series of planar images. Each of these images is a projection of the entire body mass for a particular angle, much as a common medical X-ray image. At each angle that the camera makes with the body, only radiation moving perpendicular to the camera is detected. As much of this radiation originates from various depths in the body, the result is an overlapping of the images of all elements of the body along the specific path, much in the same manner that a medical X-ray radiograph is a superposition of all anatomical structures from three dimensions into two dimensions.

An FBP study consists of many of such planar images acquired at various angles. After all the projections are acquired, they are subdivided by taking all the projections for a single, thin slice of the body at a time. All the projections for each slice are then ordered into an image called a sinogram. It represents the projection of the radiation distribution in the body for that single slice for every angle of the acquisition. The aim of the process is to retrieve the spatial distribution of the radiation from the projection data, thereby obtaining a clearer image of the body.

The quality of the image is further improved by filtering the data, which is most easily performed in the frequency domain rather than the spatial domain using well know Fast Fourier Transform techniques (FFT). The filtered data is than transformed back to the spatial domain.

The main reconstruction step involves a process known as back projection. As the original data was collected by only allowing radiation emitted perpendicular to the camera face to enter the camera, back projection smears the data from the filtered sinogram back along the same lines from where the radiation was emitted. Regions where back projection lines from different angles intersect represent areas which are of particular interest.

FBP and FFT-based reconstruction methods are popular in commercial CT scanners for their efficiency and accurate results when enough projection data is available. However, to lower the X-ray dosage (i.e., in low-dose CT imaging), the signal-to-noise ratio and the number of projections are reduced, which often results in undesirable "streaking artifacts". There are typically two main sources of streaking artifacts First, the filter may amplify the imaging noise in the sinogram, which often produces streaking lines during back projection. Second, strong sharp edges, caused by, e.g., metal or bones, are back projected along the projection direction, causing streaking artifacts, especially when the number of projections is limited. Streaking noise is signal dependent and spatial variant, often making it extremely difficult to model this artifact accurately and distinguish the noise from true edges in the image. In the field of medical radiology, this typically results in difficult and/or inconsistent clinical interpretation(s).

The second reconstruction technique mentioned above, the Iterative Reconstruction (IR) method, can often produce a better reconstruction when FBP does not yield an acceptable solution. There are a large variety of IR algorithms, but each starts with an assumed image, computes projections from the image, compares the original projection data and updates the image based upon the difference between the calculated and the actual projections. Although conceptually this approach is typically simpler than FBP, for medical applications, it has traditionally lacked the speed of implementation and accuracy. This is due to the slow convergence of the algorithm and high computational demands. For these reasons, it was superseded by the FBP method in the early development of CT.

Therefore, there remains a need to more efficiently and accurately reconstruct an image using FBP, especially in low-dose CT.

BRIEF SUMMARY OF THE INVENTION

In accordance with an embodiment of the present invention, an FBP method, referred to below as Compounded FBP (CFBP), has been developed to improve the reconstruction quality for low-dose CT scans where signal-to-noise (SNR) ratio is low and the number of projections may be restricted. The inventive method exploits complementary information from projection subsets to discriminate between angle dependent streaking noise and angle invariant true edges. This improves the image quality of the filtered back projection. The CFBP method produces image reconstruction of a quality that is typically similar to the quality of images produced by IR methods, but without the computational disadvantages of IR.

In one aspect of the invention, a method and system for constructing, from a computerized tomography (CT) scans an image relating to a physical structure involves obtaining projection data associated with the physical structure. The projection data is then divided into a plurality of subsets. FBP is then applied to each subset in the plurality of subsets. In one embodiment, an estimate of streaking noise for each subset is obtained. The image is then constructed after application of the FBP to each subset in the plurality of subsets. The estimate of streaking noise for each subset can be compared with at least some of the image after construction. In one embodiment, dependency between estimates of streaking noise for different subsets are analyzed. An independence constraint between subsets in the plurality of subsets can also be regularized.

These and other advantages of the invention will be apparent to those of ordinary skill in the art by reference to the following detailed description and the accompanying drawings

DETAILED DESCRIPTION

In one aspect of the present invention, a new FBP method results in improved reconstruction quality. The invention may be used beneficially for low dose CT scans where signal-to-noise (SNR) ratio is low and the number of projections may be restricted. As noted, this improved method is referred to herein as Compounded FBP (CFBP). The inventive method exploits complementary information from projection subsets to discriminate between angle dependent streaking noise and angle invariant true edges. To aid in understanding the invention, we will discuss below: 1. Filtered Back Projection (FBP); 2. Compounded Filtered Back Projection (CFBP); 3. CFBP Background; 4. FBP Derived from MAP Framework; and 5. CFBP Based on Cross Group Regularization.

1. Filtered Back Projection

Figure 1:
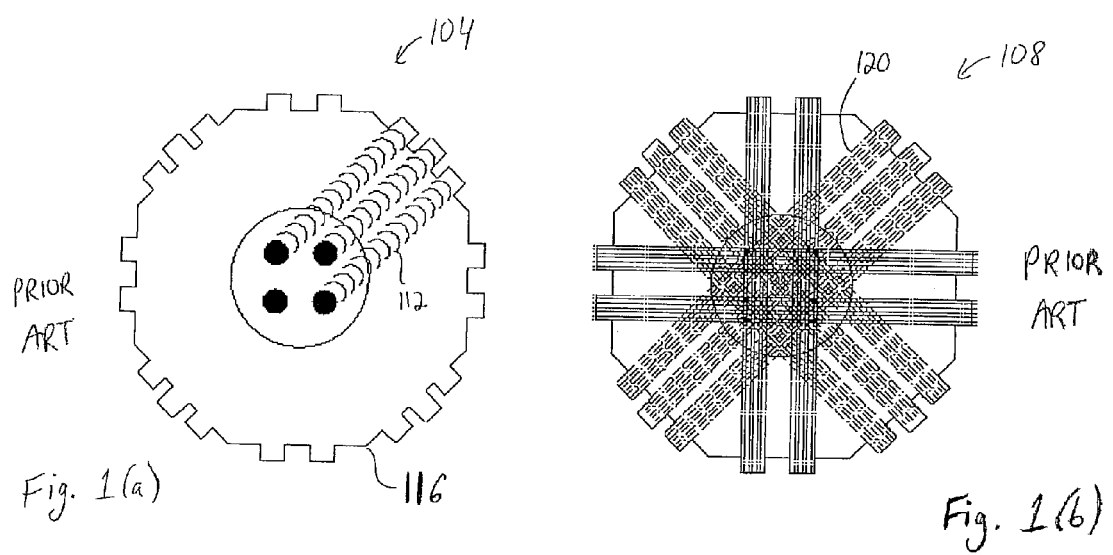
FIG. 1(a) is a prior art projection image.
FIG. 1(b) shows a prior art back projection image.

As discussed above, FBP involves the construction of an image by analyzing projection images obtained from many different viewing angles. The technique is shown schematically in FIG. 1. FIG. 1(a) shows a prior art projection image 104 and FIG. 1(b) shows a prior art back projection image 108. Assume a finite number of projections (e.g., projection 112) of an object which is illuminated with radiation. The projections of these sources at 45 degree intervals are represented on the sides of an octagon 116.

FIG. 1B illustrates back projection. Back projection is the process of running the projections (e.g., projection 120) back through the image 108 to obtain a rough approximation to the original image 104. The projections will interact constructively in regions that correspond to the sources in the original image. A problem that occurs from back projection is the blurring (star-like artifacts) that occurs in other parts of the reconstructed image. A filter may then be used to eliminate blurring. Typically, a ramp filter is used. The combination of back projection and ramp filtering is known as filtered back projection (FBP).

For parallel beam tomography, the projections can be expressed as a Radon transform of the object that is to be reconstructed. The Radon transform is defined as:

$$g(p, \theta) = R(f) = \int_{-\infty}^{\infty} \int_{-\infty}^{\infty} f(x, y) \delta(x \cos \theta + y \sin \theta - p) dx dy \qquad (2)$$

i.e., the line integral along a line (a tomography beam) at an angle $\theta$ from the y-axis and at a distance $|s|$ from the origin. By rotating the coordinate system, $$p = x \cos \theta + y \sin \theta$$

$$u = -x \sin \theta + y \cos \theta$$

$g(p,\theta)$ can be expressed as $$g(p,\theta) = \int_{-\infty}^{\infty} f(p \cos \theta - u \sin \theta, p \sin \theta + u \cos \theta) du \qquad (3)$$

In the context of tomography, the Radon transform is often called a sinogram because the Radon transform of a delta function is the characteristic function of the graph of a sine wave. Consequently, the Radon transform of a number of small objects appears graphically as a number of blurred sine waves with different amplitudes and phases.

The sinogram is a collection of raw projection data that appear as a set of sinusoidal lines and bands. A sinogram typically contains information that is not available from its reconstructed image. For instance, a full CT scanning field of view is recorded in a sinogram, whereas a small subsection or region of interest of the full field of view is usually reconstructed in an image.

In accordance with an embodiment of the present invention, compounded filtered back projection (CFBP) divides projection data into several subsets. Each subset reconstructs the same structure from a slightly different angle relative to FBP. Conventional FBP typically uses the average of these subsets.

As described in more detail below, if we define the reconstruction process as finding the most probable estimation of the true object structure being scanned, FBP can be derived from Maximum a posteriors (MAP) (i.e., an energy minimization) framework based on statistical noise/signal models. Restoration from conventional MAP does not, however, always guarantee optimal results. Better results may often be achieved by fully exploiting the complementary information provided by multiple images. In FBP, the results from different subsets of projections typically produce streaking artifacts at different orientations while the true object edges remain static. By compounding the subsets, the results of the FBP can be improved by reducing the streaking artifacts while preserving the structures (i.e., the edges). Thus, quality similar to iterative methods can effectively be obtained.

2. Compounded Filtered Back Projection

In CT imaging, cross-sectional images I (x,y) are reconstructed from their X-ray projection measurements. Without loss of generality, the projection measurements (i.e., data) (referred to above as a sinogram (i.e., g(p,θ))), are obtained by integrals along parallel rays, where θ is the angular orientation of the projection rays and p is the distance of the ray to the origin. The image reconstruction is equivalent to solving the inverse Radon transform based on the given sinogram.

Filtered back projection (FBP) is derived from signal processing theory. In one embodiment, the image can be reconstructed by first filtering each projection with a ramp filter kernel and then back projecting the P filtered projections (i.e., $g_f(p,\theta)$) into the 2D image space, as shown in the following equation.

$$\hat{I} = \sum_{k=0}^{P-1} g_f(x\cos\theta_k + y\sin\theta_k, \theta_k) \quad (1)$$

As described above, for low-dose CT imaging, where the signal-to-noise ratio is low and the number of projection is restricted, FBP reconstruction typically suffers from streaking artifacts (i.e., noise).

3. Compounded Filtered Back Projection (CFBP) Background

According to an embodiment of the present invention, a total of P projection measurements are down-sampled by a factor of M, forming M projection subsets. The conventional FBP can be reformulated using the linearity of the Radon transform.

$$\hat{I} = \sum_{m=0}^{M-1} I_m = \sum_{m=0}^{M-1} \sum_{k=0}^{P/M-1} g_f(x\cos\theta_{kM+m} + y\sin\theta_{kM+m}, \theta_{kM+m}) \quad (2)$$

where $I_m$ is the FBP reconstruction from the $m^{th}$ subset of the projections.

Since each subset of projections contains slightly different viewing angles, the streaking noise in the FBP results (i.e., $I_m$) for each subset is slightly rotated as well. Hence, the different $I_m$ are reconstructions reflecting the same underlying objects, but corrupted by differently oriented streaking noise. Therefore, the reconstruction problem can be viewed as a multi-image based restoration problem.

Unlike CFBP, conventional FBP sums all $I_m$, which is equivalent to averaging (e.g., up to a normalization factor). While the averaging process may preserve the underlying objects and reduce independent streaking noise, the reconstruction quality under low-dose imaging may still be insufficient for accurate diagnostic interpretation.

4. FBP Derived from MAP Framework

Assume that the projections are divided into two subsets (e.g., odd and even projections). A Bayesian approach (i.e., an approach that uses a statistical estimator resulting with a penalty functional that is minimized by a numerical optimization algorithm that yields the restored signal) may be used to recover the true signal based on the two sub-reconstructions (i.e., $I_1$, $I_2$) which reflect the same underlying signal but are corrupted by independent streaking noise $N_1$ and $N_2$. The problem can be formulated as follows:

$$P(\hat{I}|I_1,I_2))=c\cdot P(I_1,I_2|\hat{I})P(\hat{I})=c\cdot P_{N_1}(I_1-\hat{I})P_{N_2}(I_2-\hat{I})P_S(\hat{I}) \quad (3)$$

where c is a normalization constant and $P_{N_1}()$ is the streaking noise model. Assuming Gaussian distributed noise and uniformly distributed signal model $P_S(\hat{I})$, the Maximum a posteriori (MAP) estimation is defined as:

$$\hat{I} = \underset{\hat{I}}{\operatorname{argmin}} C(\hat{I}) = \underset{\hat{I}}{\operatorname{argmin}}(-\log(P(\hat{I}|I_1,I_2))) = \underset{\hat{I}}{\operatorname{argmin}} \sum_{i=1}^{2}(I_i - \hat{I})^2 \quad (4)$$

The cost function (i.e., the number of projections require to generate the final reconstruction) guarantees that the final reconstruction looks like the sub-reconstructions. The MAP estimation can be obtained by setting the derivative of the objection function to zero.

$$\frac{\partial C(\hat{I})}{2\partial \hat{I}} = \sum_{i=1}^{2}(I_i - \hat{I}) = 0 \Rightarrow \hat{I} = (I_1 + I_2)/2 \quad (5)$$

The MAP result is the average of the sub-reconstructions, which is the same as the traditional FBP reconstruction (as shown in Eq. 2 above).

The MAP framework does not always guarantee the optimal results. For example, the MAP framework can sometimes generate results that violate some underlying constraints, especially the independency between the streaking noise terms (i.e., the streaking noise on different sub-reconstructions does not correlate with each other due to different back projections angles). With respect to the above description, the final reconstruction is estimated as $\hat{I}=(I_1+I_2)/2$. If $\hat{I}$ is the correct reconstruction, the streaking noise on the sub-reconstruction is $$\hat{N}_1=I_1-\hat{I}=(I_1-I_2)/2=-\hat{N}_2 \quad (6)$$

As described above, the streaking noise on different sub-reconstructions does not correlate with each other due to different back projection angles. But if the average of the sub-reconstructions is used in the final reconstruction (i.e., following the traditional FBP method), the streaking noise becomes fully correlated (negative to each other). The violation of the independency constraint indicates reconstruction errors in the FBP method.

5. CFBP Based on Cross Group Regularization

By dividing the projection into sub-groups and applying FBP separately, an estimate of the streaking noise $\hat{N}_i$ in each sub-reconstruction $I_i$ can be obtained. This estimate can further be compared with the final reconstruction result $\hat{I}$. Combined with the fact that each sub-reconstruction is the true reconstruction (i.e., I) corrupted with noise (i.e., $I_i=I+N_i$), the following equation results:

$$\hat{N}_i=I_i-\hat{I}=N_i+(I-\hat{I}) \quad (7)$$

If the reconstruction $\hat{I}$ is perfect (i.e., $\hat{I}=I$), the estimated streaking noise $\hat{N}_i$ is also perfect and is independent across the sub-reconstructions. However, if a reconstruction error exists, the reconstruction error is typically equally reflected in all estimated streaking noises and can cause correlation, such as in Eq. (6). Therefore, analyzing the dependency between the estimated streaking noises can help identify and correct reconstruction errors.

In accordance with an embodiment of the present invention, the compounded filtered back projection (CFBP)

method can explicitly enforce independence between the estimated streaking noise on each sub-reconstruction.

In one embodiment, evaluating the strict independency (i.e., $p(\hat{N}_1, \hat{N}_2)=p(\hat{N}_1)p(\hat{N}_2)$) is very expensive in terms of processing time (i.e., when evaluating $p(N1, N2, \ldots Nk)$, joint histogram needs to be estimated, which increases exponentially when the number of images increases). Therefore, one of the properties of the independent random variables is instead relied upon:

$$E(h_1(\hat{N}_1)h_2(\hat{N}_2)) = E(h_1(\hat{N}_1))E(h_2(\hat{N}_2)) \quad (8)$$

where E is the expectation, and $h_1()$ and $h_2()$ are functions of $\hat{N}_1$ and $\hat{N}_2$, respectively. This equation holds for arbitrary $h_1()$ and $h_2()$, as long as the random variables $\hat{N}_1$ and $\hat{N}_2$ are independent.

For efficient computation, the functions are chosen to be a weighted sum of different order moments. For example, if $h_1(\hat{N}_1)=\hat{N}_1$ and $h_2(\hat{N}_2)=\hat{N}_2$ are chosen, the independent constraint to the uncorrelated constraint is reduced.

When the random variables are Gaussian distributed, independence and uncorrelated are equivalent. However, $\hat{N}_1$ and $\hat{N}_2$ typically do not follow a simple distribution because of the existence of restoration errors in Eq. (7). Combining higher order moments can better approximate the independence. One advantage of this approximation, based on order statistics, is that the expectations using simple summation operations can be used, which reduces the computational cost.

Therefore, a new energy term can be included for the cross group regularization to integrate with the previous MAP objective function defined in Eq. (4). The new energy term that regularizes the independence constraint between the residuals ($\hat{N}_i = I_i - \hat{I}$ and $\hat{N}_j = I_j - \hat{I}$) of sub-reconstruction i and j can be defined as:

$$e_{i,j}(\hat{N}_i, \hat{N}_j) = \|E(h_1(\hat{N}_i)h_2(\hat{N}_j)) - E(h_1(\hat{N}_i))E(h_2(\hat{N}_j))\|^2 \quad (9)$$

This regularization term is also extendable based on the available computing power and the expected accuracy of the independence evaluation. For more accurate evaluation of the independence, several terms can be added based on different choices of $h_1()$ and $h_2()$.

If the projections are divided into more sub-groups, the sum of the pairwise independence can be used to approximate the joint independence across the sub-groups. With the new cross groups regularization terms, the previous MAP framework for the reconstruction can be adapted into the following new form:

$$\hat{I} = \underset{\hat{I}}{\operatorname{argmin}} C(\hat{I}) = \underset{\hat{I}}{\operatorname{argmin}} \left( \sum_{i=1}^{M} \lambda_i (I_i - \hat{I})^2 + \lambda \sum_{j=1}^{M-1} \sum_{k=j+1}^{M} e_{j,k} \right) \quad (10)$$

The optimal solution for this objective function is not FBP any more. It can be found by setting the derivative of the objective function defined in Eq. (10) to zero. Since the new regularization terms $e_{i,j}$ is dependent on the final reconstruction result I, the optimal solution is found through several iterations.

The iteration is initialized with a loss-pass filtered FBP result $\hat{I}_0$ (i.e., the average of all sub-group reconstructions followed by a low-pass filtering). In one embodiment, two types of regions are inspected. First, for the smooth region where there are no sharp structures, the low-pass filtered FBP result provides streaking, noise-free reconstruction. The cross group regularization terms are almost at their minimum (i.e., estimated streaking noise is independent) and there is no need to refine these regions.

Second, for regions that have sharp boundaries and streaking noise, low-pass filtering removes the streaking noise and also blurs the sharp boundaries. The blurred boundaries are restoration errors and typically increase the cross group regularization cost. In one embodiment, to reduce the cost, the common part in all the sub-reconstructions are preserved while the uncorrelated part in the final reconstruction are suppressed.

Figure 2:
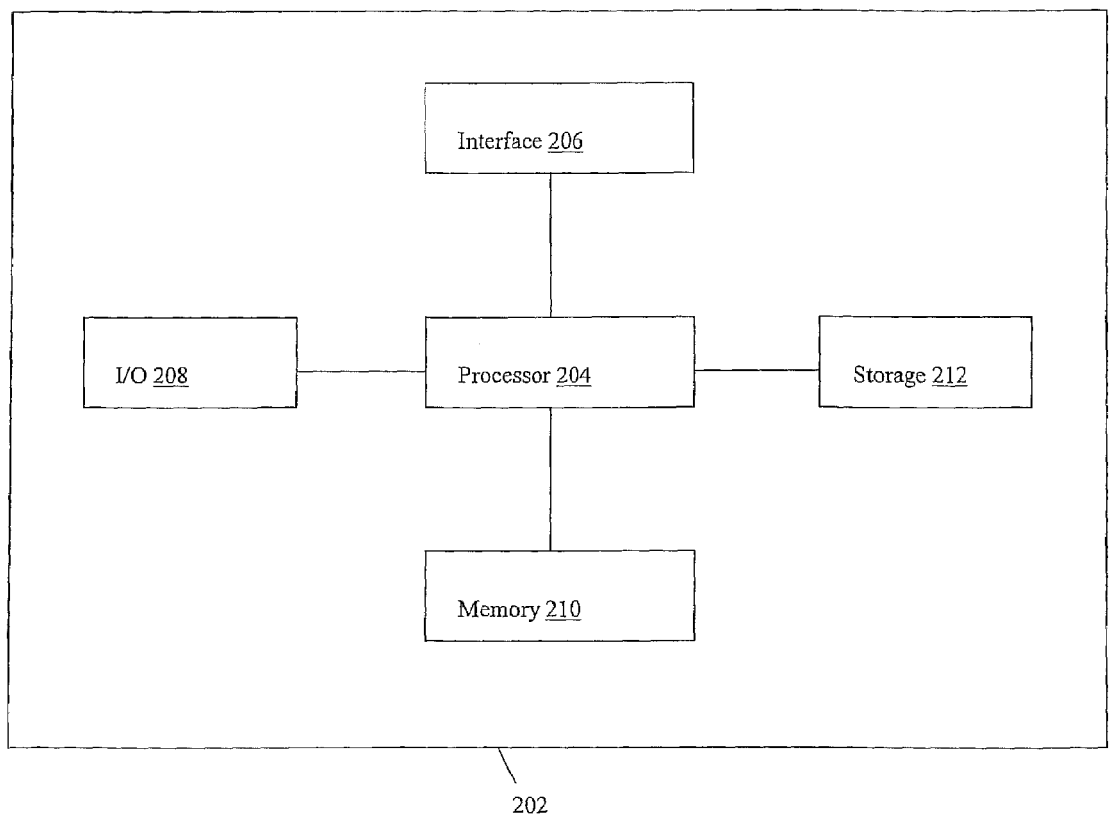
FIG. 2 shows a high level block diagram of a computer in accordance with an embodiment of the invention.

The description herewith describes the present invention in terms of the processing steps required to implement an embodiment of the invention. These steps may be performed by an appropriately programmed computer, the configuration of which is well known in the art. An appropriate computer may be implemented, for example, using well known computer processors, memory units, storage devices, computer software, and other components. A high level block diagram of such a computer is shown in FIG. 2. Computer 202 contains a processor 204 which controls the overall operation of computer 202 by executing computer program instructions which define such operation. The computer program instructions may be stored in a storage device 212 (e.g., magnetic disk) and loaded into memory 210 when execution of the computer program instructions is desired. Computer 202 also includes one or more interfaces 206 for communicating with other devices (e.g., locally or via a network). Computer 202 also includes input/output 208 which represents devices which allow for user interaction with the computer 202 (e.g., display, keyboard, mouse, speakers, buttons, etc.).

One skilled in the art will recognize that an implementation of an actual computer will contain other components as well, and that FIG. 2 is a high level representation of some of the components of such a computer for illustrative purposes. In addition, one skilled in the art will recognize that the processing steps described herein may also be implemented using dedicated hardware, the circuitry of which is configured specifically for implementing such processing steps. Alternatively, the processing steps may be implemented using various combinations of hardware and software. Also, the processing steps may take place in a computer or may be part of a larger machine.

Figure 3:
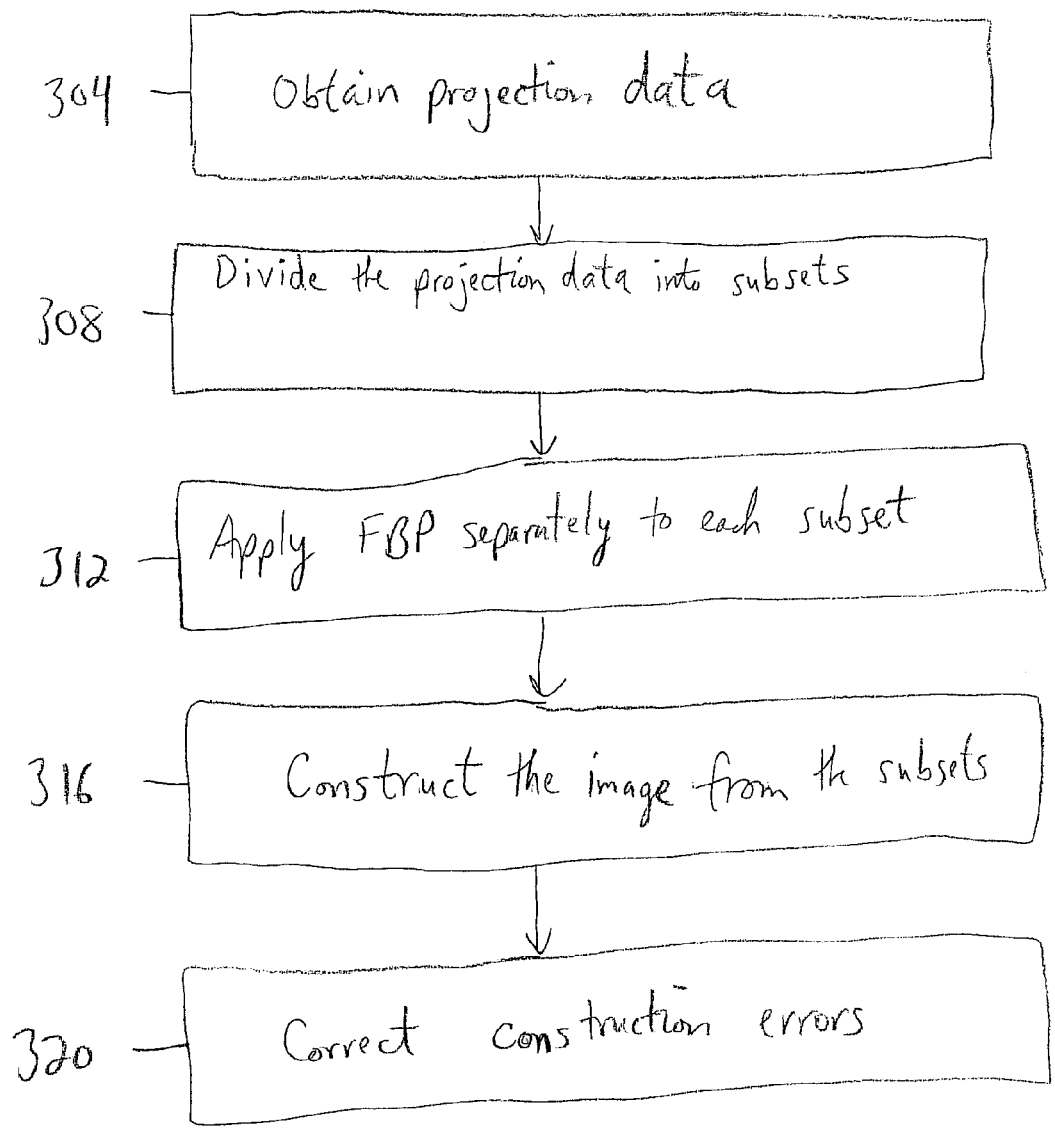
FIG. 3 is a flowchart illustrating the steps performed by the computer in accordance with an embodiment of the present invention.

FIG. 3 is a flowchart illustrating steps performed by the computer 202 in accordance with an embodiment of the present invention. Projection data associated with a physical structure is first obtained in step 304. The projection data is then divided into subsets in step 308. Filtered back projection is then applied separately to each subset in step 312, and the image is subsequently constructed (i.e., reconstructed) from the subsets in step 316. Construction errors are then corrected in step 320, such as by including the new regularization term for the cross group regularization as described above.

Figure 4:
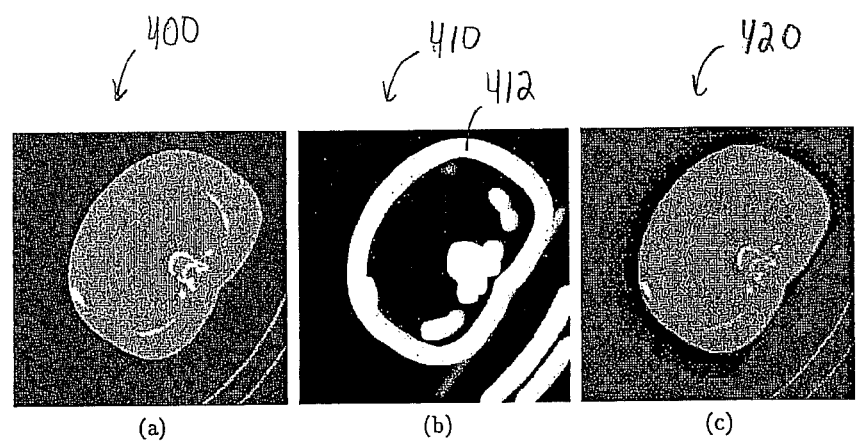
FIG. 4(a) is an image of FBP reconstruction from all projections.
FIG. 4(b) shows an image illustrating a regularization term in the first iteration in accordance with an embodiment of the present invention.
FIG. 4(c) shows an image of the regularized CFBP reconstruction result in accordance with an embodiment of the present invention.

FIGS. 4(a)-4(c) illustrate FBP reconstruction in accordance with an embodiment of the present invention. In particular, FIG. 4(a) shows an image 400 of FBP reconstruction from all projections. FIG. 4(b) shows an image 410 illustrating the regularization term in the first iteration. FIG. 4(c) illustrates an image 420 of the regularized CFBP reconstruction result.

In one embodiment, the approximated independence evaluation based on order statistics and summation operation reduces the computational cost of the regularization term. This allows efficient minimization of the objective function iteratively.

Figure 5:
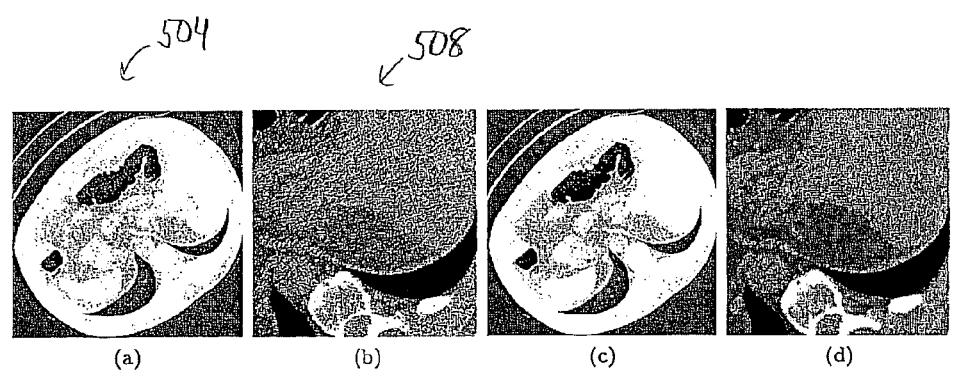
FIG. 5(a) is a reconstructed image from all projections in accordance with an embodiment of the invention.
FIG. 5(b) is an enlarged image of the FBP result with streaking noise.
FIG. 5(c) is a regularized CFBP reconstruction result in accordance with an embodiment of the present invention.
FIG. 5(d) is an enlarged image of the CFBP reconstruction result in accordance with an embodiment of the present invention.

FIGS. 5(a) and 5(b) illustrate an entire reconstructed image as well as an enlarged part of the FBP result with streaking noise. In one embodiment, the compounded filtered back projection method is applied to several low dose CT scans. For example, in a first data set, a sinogram with 100 projections and 367 detectors per projection is used. The dimensions of the reconstructed image are 258 by 258. Filtered back projection of the original sinogram yields a reconstruction with apparent streaking noise as shown in FIG. 4(a). The streaking noise typically interwinds with underlying object structures, obscuring the true structures.

The CFBP method is then applied, as shown in Eq. (10), with cross group regularization constraints. The projections are divided into two subsets and two images are reconstructed using FBP on each of the subsets. To initialize the iterative optimization scheme, the initial reconstruction result is assigned to be the averaging of the two sub-group FBP results followed by uniform low-pass filtering. The streaking noise is reduced by the low-pass filtering, which is equivalent to the FBP modulated by a strong low-pass windowing function. The sharp boundaries, however, may also be blurred.

In accordance with an embodiment of the present invention, the regularization term of the CFBP method captures the reconstruction error around the sharp boundaries in the initial guess. This is shown in FIG. 4(b), where the white lines (e.g., line 412) represents high cross group dependencies.

The regularization term is estimated based on the pixels within a neighborhood of each pixel location and hence cover a (e.g., slightly) larger region than the true boundaries. This does not, however, typically affect the sharpness of the reconstruction result. The final reconstruction, shown in image 420 of FIG. 4(c), shows an image having its noise removed while even weak edges are well preserved.

In another embodiment, the CFBP method is applied to another low-dose CT data set consisting of 580 projections and 1344 detectors per projection. The dimensions of the reconstructed image are 949 by 949.

FIG. 5(a) illustrates the reconstructed image 504 from all projections. FIG. 5(b) illustrates an enlarged image 508 of the FBP result with streaking noise. For CFBP, the projection is divided into four subsets. The CFBP results are shown in FIGS. 5(c) and 5(d). In particular, FIG. 5(c) illustrates a regularized CFBP reconstruction result 512. FIG. 5(d) illustrates an enlarged image 516 of the CFBP reconstruction result. From this enlarged image 516, the reduction of the streaking noise and the good preservation of the sharp structures is shown.

Figure 6:
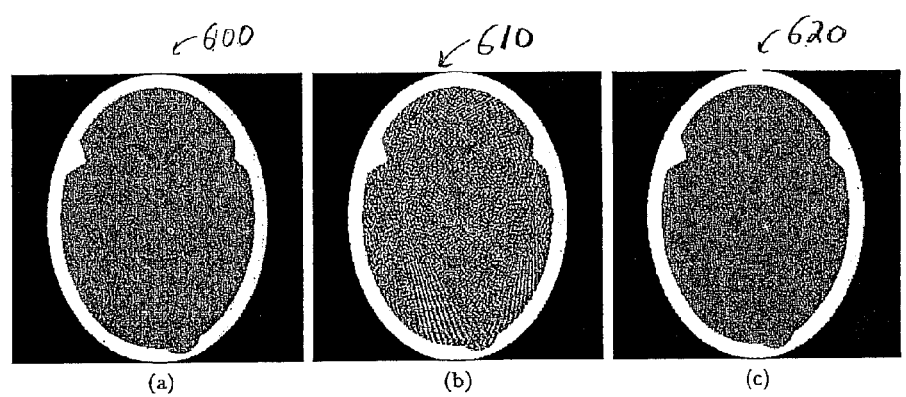
FIG. 6(a) is an original image for reconstruction.
FIG. 6(b) is an FBP reconstruction image from all projections in accordance with an embodiment of the present invention.
FIG. 6(c) is a CFBP reconstruction result in accordance with an embodiment of the present invention.

A quantitative analysis can also be performed. FIG. 6(a) is an original image 600, and FIG. 6(b) is an FBP reconstruction image 610 from all projections. FIG. 6(c) illustrates a CFBP reconstruction result 620. An exemplary comparison can be performed on a 258 by 258 phantom image with 100 projections. The projection data was corrupted with additive white Gaussian noise of variance 1. FBP yields an image 600 with streaking noise, as shown in FIG. 6(a). The proposed CFBP with five subsets shows noise reduction in image 610 of FIG. 6(b) and a CFBP reconstruction result 620 in FIG. 6(c).

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for constructing, from a computerized tomography scan, an image relating to a physical structure, comprising:
    obtaining projection data associated with the physical structure;
    dividing said projection data into a plurality of subsets;
    applying filtered back projection (FBP) to each subset in said plurality of subsets to generate a plurality of sub-reconstructions, wherein each sub-reconstruction is an entire reconstruction of said image based on a respective subset in said plurality of subsets; and
    constructing said image based on the said plurality of sub-reconstructions generated based on said plurality of subsets.

2. The method of claim 1 wherein said applying FBP to each subset further comprises obtaining an estimate of streaking noise for each sub-reconstruction.

3. The method of claim 2 further comprising comparing said estimate of streaking noise for each sub-reconstruction with at least a portion of said constructed image.

4. The method of claim 3 further comprising analyzing dependency between estimates of streaking noise for different sub-reconstructions.

5. The method of claim 1 further comprising regularizing an independence constraint between sub-reconstructions in said plurality of sub-reconstructions.

6. The method of claim 5 wherein said regularizing an independence constraint further comprises including a regularization term defined in the following equation:

$$e_{i,j}(\hat{N}_i,\hat{N}_j) = \|E(h_1(\hat{N}_i)h_2(\hat{N}_j)) - E(h_1(\hat{N}_i))E(h_2(\hat{N}_j))\|^2$$

where E is the expectation, $\hat{N}_i$ and $\hat{N}_j$ are random variables, and $h_1(\ )$ and $h_2(\ )$ are functions of $\hat{N}_i$ and $\hat{N}_j$, respectively.

7. The method of claim 6 wherein said constructing is formed from an energy minimization framework.

8. The method of claim 1 wherein said obtaining said projection data further comprises solving integrals along parallel rays directed along and through said image.

9. The method of claim 1 wherein said dividing of said projection data into a plurality of subsets further comprises down-sampling at least a portion of said projection data by a predetermined factor.

10. A system for constructing, from a computerized tomography scan, an image relating to a physical structure, comprising:
    means for obtaining projection data associated with said physical structure;
    means for dividing said projection data into a plurality of subsets;
    means for applying filtered back projection (FBP) to each subset in said plurality of subsets to generate a plurality of sub-reconstructions, wherein each sub-reconstruction is an entire reconstruction of said image based on a respective subset in said plurality of subsets; and
    means for constructing said image based on the said plurality of sub-reconstructions generated based on said plurality of subsets.

11. The system of claim 10 wherein said means for applying FBP to each subset further comprises means for obtaining an estimate of streaking noise for each sub-reconstruction.

12. The system of claim 11 further comprising means for comparing said estimate of streaking noise for each sub-reconstruction with at least a portion of said image after construction.

13. The system of claim 12 further comprising means for analyzing dependency between estimates of streaking noise for different sub-reconstructions.

14. The system of claim 10 further comprising means for regularizing an independence constraint between sub-reconstructions in said plurality of sub-reconstructions.

15. The system of claim 14 wherein said means for regularizing an independence constraint further comprises means for including a regularization term defined in the following equation:

$$e_{i,j}(\hat{N}_i,\hat{N}_j)=\|E(h_1(\hat{N}_i)h_2(\hat{N}_j))-E(h_1(\hat{N}_i))E(h_2(\hat{N}_j))\|^2$$

where E is the expectation, $\hat{N}_i$ and $\hat{N}_j$ are random variables, and $h_1(\ )$ and $h_2(\ )$ are functions of $\hat{N}_i$ and $\hat{N}_j$, respectively.

16. The system of claim 15 wherein said means for constructing is formed from an energy minimization framework.

17. The system of claim 10 wherein said means for obtaining said projection data further comprises means for solving integrals along parallel rays.

18. The system of claim 10 wherein said means for dividing of said projection data into a plurality of subsets further comprises means for down-sampling at least a portion of said projection data by a predetermined factor.

19. A computer readable medium comprising computer program instructions capable of being executed in a processor and defining the steps comprising:
  obtaining projection data associated with a physical structure;
  dividing said projection data into a plurality of subsets;
  applying filtered back projection (FBP) to each subset in said plurality of subsets to generate a plurality of sub-reconstructions, wherein each sub-reconstruction is an entire reconstruction of said image based on a respective subset in said plurality of subsets; and
  constructing an image based on the said plurality of sub-reconstructions generated based on said plurality of subsets.

20. The computer readable medium of claim 19 wherein said applying FBP to each subset further comprises the step of obtaining an estimate of streaking noise for each sub-reconstruction.

21. The computer readable medium of claim 20 further comprising the step of comparing said estimate of streaking noise for each sub-reconstruction with at least a portion of said constructed image.

22. The computer readable medium of claim 21 further comprising the step of analyzing dependency between estimates of streaking noise for different sub-reconstructions.

23. The computer readable medium of claim 19 further comprising the step of regularizing an independence constraint between sub-reconstructions in said plurality of sub-reconstructions.

24. The computer readable medium of claim 23 wherein said regularizing an independence constraint further comprises including a regularization term defined in the following equation:

$$e_{i,j}(\hat{N}_i,\hat{N}_j)=\|E(h_1(\hat{N}_i)h_2(\hat{N}_j))-E(h_1(\hat{N}_i))E(h_2(\hat{N}_j))\|^2$$

where E is the expectation, $\hat{N}_i$ and $\hat{N}_j$ are random variables, and $h_1(\ )$ and $h_2(\ )$ are functions of $\hat{N}_i$ and $\hat{N}_j$, respectively.

25. The computer readable medium of claim 24 wherein said step of constructing is formed from an energy minimization framework.

26. The computer readable medium of claim 19 wherein said step of obtaining said projection data further comprises solving integrals along parallel rays directed along and through said image.

27. The computer readable medium of claim 19 wherein said dividing of said projection data into a plurality of subsets further comprises the step of down-sampling at least a portion of said projection data by a predetermined factor.

* * * * *